United States Patent
Kim et al.

(10) Patent No.: US 12,387,832 B2
(45) Date of Patent: Aug. 12, 2025

(54) USER AWARE MICROCURRENT THERAPY DEVICE

(71) Applicant: Lee Sol Co., Ltd., Seoul (KR)

(72) Inventors: Moonsoo Kim, Gyeonggi-do (KR); Seung Woo Lee, Seoul (KR)

(73) Assignee: Lee Sol Co., Ltd., Seoul (KR)

( * ) Notice: Subject to any disclaimer, the term of this patent is extended or adjusted under 35 U.S.C. 154(b) by 557 days.

(21) Appl. No.: 17/405,479

(22) Filed: Aug. 18, 2021

(65) Prior Publication Data

US 2022/0351827 A1    Nov. 3, 2022

(30) Foreign Application Priority Data

Apr. 28, 2021    (KR) .......................... 10-2021-0054872

(51) Int. Cl.
*G16H 20/40* (2018.01)
*A61B 5/00* (2006.01)
(Continued)

(52) U.S. Cl.
CPC .............. *G16H 20/40* (2018.01); *A61B 5/74* (2013.01); *A61N 1/18* (2013.01); *A61N 1/36139* (2013.01);
(Continued)

(58) Field of Classification Search
CPC .............. A61N 1/3727; A61N 1/37247; A61N 1/37258; A61N 1/36139; A61N 1/36167
See application file for complete search history.

(56) References Cited

U.S. PATENT DOCUMENTS

2011/0172735 A1* 7/2011 Johari ................ A61N 1/36025
607/48
2012/0265105 A1* 10/2012 Tsutsui .............. A61H 23/0245
601/2
(Continued)

FOREIGN PATENT DOCUMENTS

KR         102013008         7/2013
KR         101340691         12/2013
(Continued)

OTHER PUBLICATIONS

English Translation of KR 1020130081426 (Year: 2013).*

*Primary Examiner* — Rex R Holmes
*Assistant Examiner* — Moussa Haddad
(74) *Attorney, Agent, or Firm* — Sughrue Mion, PLLC

(57) ABSTRACT

Disclosed is a user aware microcurrent therapy device with improved reliability of microcurrent therapy so that a user can determine an operation of the microcurrent therapy device. The user aware microcurrent therapy device may include a controller which is input with first input data for turning on/off power, second input data for setting generation times and periods of a microcurrent for microcurrent therapy and an aware stimulus which notifies the user of the generation of the microcurrent, and third input data for setting generation types of the microcurrent and the aware stimulus; a microcurrent generator which is connected to the controller to generate a specific type of microcurrent separated into a plurality of periods according to the second and third input data input to the controller for a predetermined time; an aware stimulus generator which is connected to the controller to generate a specific type of aware stimulus separated into a plurality of periods according to the second and third input data input to the controller alternately with the microcurrent for a predetermined time; and a plurality of electrodes which is attached to a part of the user's body to (Continued)

apply the microcurrent generated by the microcurrent generator or the aware stimulus generated by the aware stimulus generator to the user.

8 Claims, 4 Drawing Sheets

(51) Int. Cl.
    *A61N 1/18*         (2006.01)
    *A61N 1/36*         (2006.01)
    *A61N 1/372*       (2006.01)
    *G16H 40/63*      (2018.01)

(52) U.S. Cl.
    CPC ..... *A61N 1/36167* (2013.01); *A61N 1/37247* (2013.01); *A61N 1/37258* (2013.01); *A61N 1/3727* (2013.01); *G16H 40/63* (2018.01)

(56) References Cited

U.S. PATENT DOCUMENTS

| | | | |
|---|---|---|---|
| 2014/0121572 A1* | 5/2014 | Nathanson | A61N 1/328 601/21 |
| 2017/0189227 A1* | 7/2017 | Brunson | A61N 1/325 |
| 2017/0266446 A1* | 9/2017 | O'Clock | A61N 1/36046 |
| 2018/0133470 A1* | 5/2018 | Park | A61N 5/0616 |
| 2019/0321622 A1* | 10/2019 | Samejima | A61N 1/3603 |
| 2023/0338729 A1* | 10/2023 | Chi | A61N 1/32 |

FOREIGN PATENT DOCUMENTS

| | | |
|---|---|---|
| KR | 1020130104870 | 3/2014 |
| KR | 101777338 | 9/2017 |
| KR | 102092375 | 5/2020 |
| KR | 1020200062497 | 6/2020 |
| KR | 102141761 | 8/2020 |

\* cited by examiner

USER AWARE MICROCURRENT THERAPY DEVICE

CROSS-REFERENCE TO RELATED APPLICATIONS

This application claims the priority of Korean Patent Application No. 2021-0054872 filed on Apr. 28, 2021, in the Korean Intellectual Property Office, the disclosure of which is incorporated herein by reference.

BACKGROUND

Field

The present disclosure relates to a user aware microcurrent therapy device, and more particularly, to a user aware microcurrent therapy device with improved reliability of microcurrent therapy so that a user may determine an operation of the microcurrent therapy device.

Description of the Related Art

In general, electrical therapy is also known as an electrotherapy as a method for treating various diseases by communicating with a microcurrent in a human body. The functions or uses of the electrical therapy vary depending on the waveform of a frequency, the intensity of a current, an applied site, etc.

In other words, in the electrical therapy, a high-frequency therapy device and a low-frequency therapy device have been frequently developed and used depending on a frequency to be applied. A low-frequency electrical therapy uses a frequency of several Hz to 1,000 Hz, a medium-frequency electrical therapy uses 1 KHz to 10 KHz, and a high-frequency electrical therapy uses a frequency of 100 KHz or more.

In addition, in the therapy device, which is used for pain relief and the recovery of various musculoskeletal disorders such as back pain, arthritis, spondylitis, and sports injuries, electrical therapy such as a medium frequency, a high frequency, and the like, ultrasonic and phototherapy devices, and the like have been introduced. The ultrasonic therapy is used for treatment such as recovery of soft tissue damage by using a frequency of 20 KHz to 10 MHz, applying vibration to a human deep tissue, and using a heat effect.

Furthermore, recently, a microcurrent therapy device has been frequently applied and used to the human body for treatment by inducing and applying a microcurrent to the human body according to adjustment of the output intensity within a range of about 10 μA to 500 μA or more.

Conventional microcurrent therapy devices induce and apply the microcurrent in the human body to help blood circulation, promote metabolism, relieve pain in human body, and have an effect of treatment and prevention of musculoskeletal diseases, and have been used for skin beauty by improving fatigue recovery and blood circulation, and help in weight loss to have a health promotion effect.

As prior arts related to the microcurrent therapy device, there are disclosed Korean patent registration No. 10-2092375 (hereinafter referred to as 'Prior Art 1') and Korean patent registration No. 10-1340691 (hereinafter referred to as 'Prior Art 2').

In Prior Art 1, there is provided a microcurrent pain therapy device combined with a low output laser which includes a body provided in a gripping form, a laser treatment module which is provided on one side of a contact surface of the body to be in contact with the skin and outputs a therapy laser; and a current treatment module provided on the other side of the contact surface of the body to be adjacent with the laser treatment module and generates a treatment current. At this time, the laser treatment module includes a plurality of first diodes having a first wavelength, a plurality of second diodes having a second wavelength relatively larger than the first wavelength, and a plurality of third diodes having a third wavelength relatively larger than the second wavelength, in which the plurality of second diodes is arranged to form a triangle and the plurality of third diodes is arranged to form a reverse triangle corresponding to the triangle, in which the triangle and the reverse triangle share a central point.

However, in Prior Art 1, there is a problem that since there is provided no means capable of notifying a user of whether the microcurrent is applied to the user during the microcurrent treatment, the user cannot determine whether the microcurrent therapy device is operated, thereby deteriorating the reliability of the microcurrent treatment.

In Prior Art 2, there is provided a microcurrent therapy device using a high electric potential which includes a power unit supplying commercial AC power, an operation unit inputting a frequency operation signal corresponding to a user's treatment site condition, a control unit generating a relay control signal and a high electric potential current control signal according to the frequency set by the operation unit, a relay unit supplying or cutting off the commercial AC power supplied from the power unit according to the relay control signal generated by the control unit, a high voltage output unit outputting a high electric potential by boosting up the commercial AC power outputted from the relay unit, and a current regulating unit regulating the high electric potential current outputted from the high voltage output unit according to the current control signal generated by the control unit in response to the user's treatment site condition.

However, in Prior Art 2, unlike Prior Art 1, there is provided a display unit displaying an operation state in the microcurrent therapy device, but in the microcurrent therapy device of Prior Art 2, there is a problem that since the volume thereof is increased by the display unit, portability deteriorates.

As a result, there is a need to develop a microcurrent therapy device with improved reliability so that the user can determine the operation of the microcurrent therapy device even while portability is excellent due to a simple configuration.

SUMMARY

An object to be achieved by the present disclosure is to provide a user aware microcurrent therapy device capable of improving reliability of microcurrent therapy by applying an aware stimulus to a user so that the user can determine an operation of the microcurrent therapy device while having excellent portability due to a simple configuration.

Another object to be achieved by the present disclosure is to provide a user aware microcurrent therapy device capable of easily being aware of the start and end of the microcurrent therapy by the user by varying amplitudes and/or wavelengths of an aware stimulus period for notifying the start and end of the microcurrent therapy and remaining aware stimulus periods generated in the microcurrent therapy process.

Meanwhile, the technical objects to be achieved in the present disclosure are not limited to the aforementioned technical objects, and other technical objects, which are not mentioned above, will be apparently understood to a person having ordinary skill in the art from the following description.

According to a first aspect of the present disclosure, there is provided a user aware microcurrent therapy device. The user aware microcurrent therapy device may include a controller which is input with first input data for turning on/off power, second input data for setting generation times and periods of a microcurrent for microcurrent therapy and an aware stimulus which notifies the user of the generation of the microcurrent, and third input data for setting generation types of the microcurrent and the aware stimulus; a microcurrent generator which is connected to the controller to generate a specific type of microcurrent separated into a plurality of periods according to the second and third input data input to the controller for a predetermined time; an aware stimulus generator which is connected to the controller to generate a specific type of aware stimulus separated into a plurality of periods according to the second and third input data input to the controller alternately with the microcurrent for a predetermined time; and a plurality of electrodes which is attached to a part of the user's body to apply the microcurrent generated by the microcurrent generator or the aware stimulus generated by the aware stimulus generator to the user.

According to a second aspect of the present disclosure, there is provided a user aware microcurrent therapy device. The user aware microcurrent therapy device may include a controller which is input with first input data for turning on/off power, second input data for setting generation times and periods of a microcurrent for microcurrent therapy and an aware stimulus which notifies the user of the generation of the microcurrent, and third input data for setting generation types of the microcurrent and the aware stimulus; a microcurrent/aware stimulus generator which is connected to the controller to generate a specific type of microcurrent separated into a plurality of periods according to the second and third input data input to the controller for a predetermined time and generate a specific type of aware stimulus separated into a plurality of periods alternately with the microcurrent for a predetermined time; and a plurality of electrodes which is attached to a part of the user's body to apply the microcurrent or the aware stimulus generated by the microcurrent/aware stimulus generator to the user.

According to a third aspect of the present disclosure, there is provided a user aware microcurrent therapy device. The user aware microcurrent therapy device may include a controller which is input with first input data for turning on/off power, second input data for setting generation times and periods of a microcurrent for microcurrent therapy and an aware stimulus which notifies the user of the generation of the microcurrent, and third input data for setting generation types of the microcurrent and the aware stimulus; a microcurrent generator which is connected to the controller to generate a specific type of microcurrent in one period according to the second and third input data input to the controller for a predetermined time; an aware stimulus generator which is connected to the controller to generate a specific type of aware stimulus in one period or separated into a plurality of periods according to the second and third input data input to the controller for a predetermined time; a plurality of microcurrent electrodes which is attached to a part of the user's body to apply the microcurrent generated by the microcurrent generator to the user; and a plurality of aware stimulus electrodes which is attached to a part of the user's body except for the part attached with the plurality of microcurrent electrodes to apply the aware stimulus generated by the aware stimulus generator to the user.

The controller may set generation types of the microcurrent and the aware stimulus to at least one of a direct current, an alternating current, and a pulsed current when the third input data is input.

The controller may first set the generation type of the microcurrent through the input of the third input data and set the generation type of the aware stimulus with a different amplitude and/or a different wavelength from the generation type of the microcurrent when the generation type of the microcurrent is set.

The controller may set the generation type of the aware stimulus so that a start period of the aware stimulus for notifying the start of the microcurrent therapy and an end period of the aware stimulus for notifying the end of the microcurrent therapy are generated with different amplitudes and/or different wavelengths from the remaining periods of the aware stimulus based on a case where the aware stimulus is separated into a plurality of periods.

The controller may set the generation type of the aware stimulus so that a virtual value amplitude of the start period of the aware stimulus is different from that of the end period of the aware stimulus.

The controller may set generation times and periods of the microcurrent and the aware stimulus so that the period of the microcurrent is generated earlier than the period of the aware stimulus when the microcurrent therapy starts in the case where the second input data is input.

The controller may set the generation times and periods of the microcurrent and the aware stimulus so that an end period of the aware stimulus for notifying that the microcurrent therapy ends in the periods of the aware stimulus separated into plural ends and then the microcurrent therapy ends, when the second input data is input.

The controller may set the generation times and periods of the microcurrent and the aware stimulus so that the period of the microcurrent and the period of the aware stimulus separated into plural through the input of the second input data are gradually increased as the microcurrent therapy is performed.

The controller may set the generation times and periods of the microcurrent and the aware stimulus so that the period of the microcurrent and the period of the aware stimulus separated into plural through the input of the second input data are gradually decreased as the microcurrent therapy is performed.

According to the present disclosure, it is possible to improve the reliability of microcurrent therapy by allowing a user to determine an operation of a microcurrent therapy device.

Further, it is possible to provide effective microcurrent therapy by allowing a user to determine the start and end of the microcurrent therapy through an aware stimulus.

Effects which can be obtained in the present disclosure are not limited to the aforementioned effects and other unmentioned effects will be clearly understood by those skilled in the art from the following description.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE PREFERRED EMBODIMENT

Figure 1:
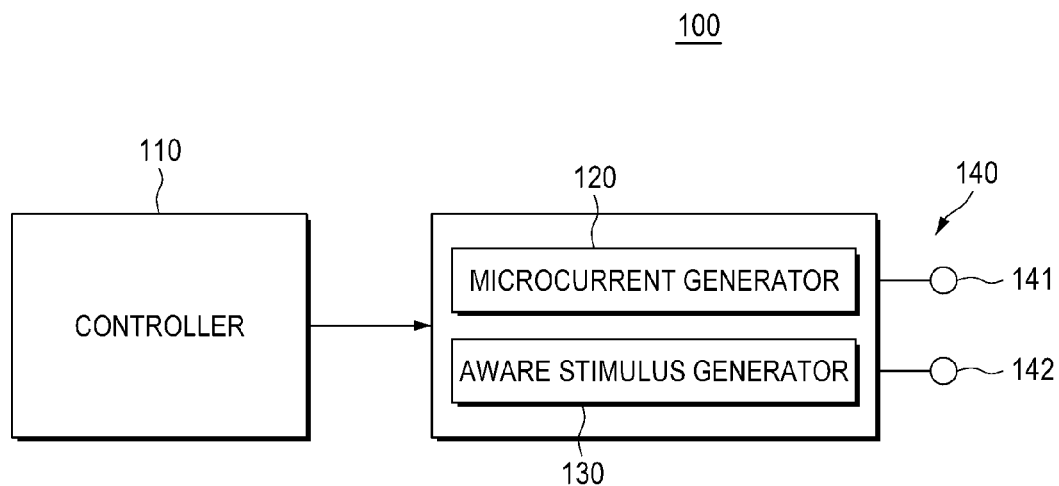
FIG. 1 is a schematic diagram of a user aware microcurrent therapy device according to a first exemplary embodiment of the present disclosure.

Hereinafter, exemplary embodiments of the present disclosure will be described in detail so as to be easily implemented by those skilled in the art, with reference to the accompanying drawings. A description of the present disclosure is merely an exemplary embodiment for a structural or functional description and the scope of the present disclosure should not be construed as being limited by exemplary embodiments described in a text. That is, since the exemplary embodiment can be variously changed and have various forms, the scope of the present disclosure should be understood to include equivalents capable of realizing the technical spirit. Further, it should be understood that since a specific exemplary embodiment should not include all objects or effects or include only the effect, the scope of the present disclosure is not limited by the object or effect.

Meanings of terms described in the present disclosure should be understood as follows.

The terms "first", "second", and the like are used to differentiate a certain component from other components, but the scope of the rights should not be construed to be limited by the terms. For example, a first component may be referred to as a second component, and similarly, the second component may be referred to as the first component. It should be understood that, when it is described that a component is "connected to" the other component, the component may be directly connected to the other component or another component may be present therebetween. In contrast, it should be understood that when it is described that a component is "directly connected to" the other component, another component is not present therebetween. Meanwhile, other expressions describing the relationship between the components, that is, expressions such as "between" and "directly between" or "adjacent to" and "directly adjacent to" should be similarly interpreted.

It is to be understood that the singular expression encompasses a plurality of expressions unless the context clearly dictates otherwise and it should be understood that the term "including" or "having" indicates that a feature, a number, a step, an operation, a component, a part, or the combination thereof described in the specification is present, but does not exclude a possibility of presence or addition of one or more other features, numbers, steps, operations, components, parts or combinations thereof, in advance.

If it is not contrarily defined, all terms used herein have the same meanings as those generally understood by those skilled in the art. Terms which are defined in a generally used dictionary should be interpreted to have the same meaning as the meaning in the context of the related art, and are not interpreted as an ideal meaning or excessively formal meanings unless clearly defined in the present disclosure.

Hereinafter, a user aware microcurrent therapy device 100 according to a first exemplary embodiment of the present disclosure will be described in detail.

Figure 2:
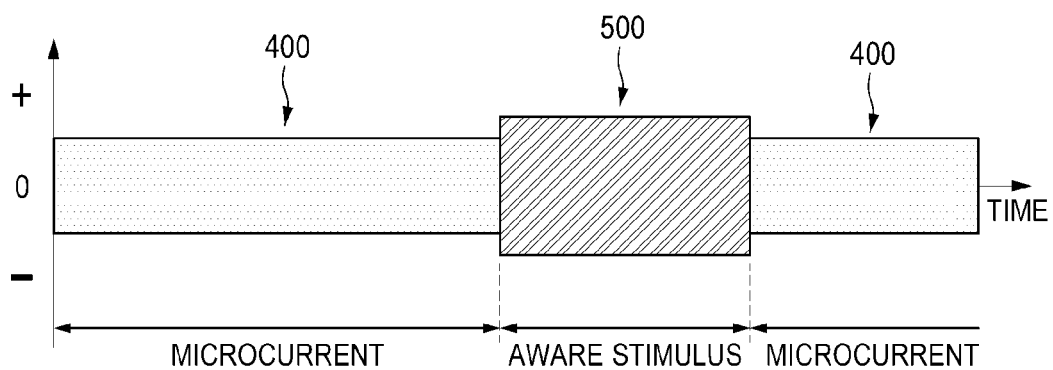
FIG. 2 is a graph showing periods of microcurrents and aware stimuli which are alternately generated according to first and second exemplary embodiments of the present disclosure.

FIG. 1 is a schematic diagram of a user aware microcurrent therapy device according to a first exemplary embodiment of the present disclosure and FIG. 2 is a graph showing periods of microcurrents and aware stimuli which are alternately generated according to first and second exemplary embodiments of the present disclosure.

Referring to FIGS. 1 and 2, the user aware microcurrent therapy device 100 according to the first exemplary embodiment of the present disclosure includes a controller 110, a microcurrent generator 120, an aware stimulus generator 130, and a plurality of electrodes 140.

The controller 110 controls an operation of the microcurrent generator 120 and the aware stimulus generator 130 when input data is input by a user directly or in remote control.

The input data input to the controller 110 may be, as a specific example, first input data for turning on/off power, second input data for setting generation times and periods of a microcurrent 400 for microcurrent therapy and an aware stimulus 500 which notifies the user of the generation of the microcurrent, and third input data for setting generation types of the microcurrent 400 and the aware stimulus 500.

When the microcurrent therapy starts according to the input of the second input data, as the graph shown in FIG. 2, the controller 110 sets generation times and periods of the microcurrent 400 and the aware stimulus 500 so that the period of the microcurrent 400 is generated earlier than the period of the aware stimulus 500.

Further, the controller 110 sets the generation times and the periods of the microcurrent 400 and the aware stimulus 500 so that the microcurrent therapy ends after an end period of the aware stimulus 500 for notifying that the microcurrent therapy ends in periods of the aware stimulus 500 separated into plural ends according to the input of the second data.

Furthermore, when the microcurrent 400 and the aware stimulus 500 are separated into a plurality of periods, the controller 110 may set the generation times and the periods of the microcurrent 400 and the aware stimulus 500 so that the periods of the microcurrent 400 and the aware stimulus 500 are gradually increased or decreased through the input of the second input data while the microcurrent therapy is performed.

The microcurrent generator 120 is connected to the controller 110 to turn on/off the power according to the first input data, and generates a specific type of microcurrent 400 for a predetermined time according to the second and third input data when the power is turned on.

At this time, the microcurrent 400 means a current which cannot be aware by the user who receives the microcurrent therapy and is separated into a plurality of periods to be alternately generated with the aware stimulus 500 as the graph shown in FIG. 2 in the microcurrent therapy process.

The aware stimulus generator 130 is connected to the controller 110 to turn on/off the power according to the first input data, and generates a specific type of aware stimulus 500 for a predetermined time according to the second and third input data when the power is turned on.

At this time, the aware stimulus 500 means a current which can be aware by the user who receives the microcurrent therapy and is generated alternately with the microcurrent 400 in the microcurrent therapy process to notify the user that the microcurrent 400 is generated in the microcurrent generator 120, and is separated into a plurality of periods to be alternately generated with the microcurrent 400 as the graph shown in FIG. 2.

The plurality of electrodes 140 may consist of a microcurrent electrode 141 and an aware stimulus electrode 142 which are attached to a part of the user's body. The plurality of electrodes 140 may consist of electrodes which are smaller than or larger than the microcurrent electrode 141 and the aware stimulus electrode 142, but in the present disclosure, the plurality of electrodes 140 will be described as the microcurrent electrode 141 and the aware stimulus electrode 142.

The microcurrent electrode 141 is connected with the microcurrent generator 120 so that the microcurrent 400 generated by the microcurrent generator 120 flows. As a result, when the microcurrent electrode 141 is attached to a user's body part to receive the microcurrent therapy, the microcurrent electrode 141 applies a specific type of microcurrent 400 separated into the plurality of periods to the body part.

The aware stimulus electrode 142 is connected with the aware stimulus generator 130 so that the aware stimulus 500 generated by the aware stimulus generator 130 flows. As a result, when the aware stimulus electrode 142 is attached to the remaining body parts except for the user's body part attached with the microcurrent electrode 141, the aware stimulus electrode 142 applies a specific type of aware stimulus 500 separated into the plurality of periods to be generated alternately with the microcurrent 400 to the body part.

Through the microcurrent electrode 141 and the aware stimulus electrode 142, while the user receives the microcurrent therapy by the microcurrent 400, the user may determine whether the microcurrent therapy is performed through the aware stimulus 500 generated alternately with the microcurrent 400.

Figure 3:
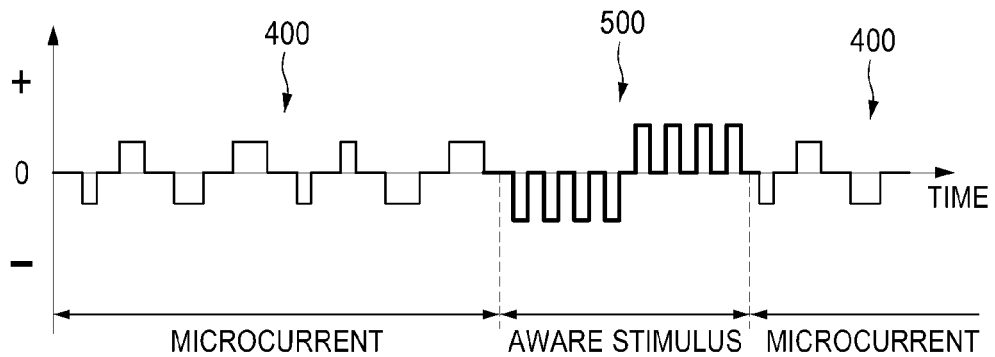
FIG. 3 is a graph showing waveforms of the microcurrents and the aware stimuli according to the first and second exemplary embodiments of the present disclosure.

FIG. 3 is a graph showing waveforms of the microcurrents and the aware stimuli according to the first and second exemplary embodiments of the present disclosure.

Referring to FIG. 3, the controller 110 may set the generation types of the microcurrent 400 and the aware stimulus 500 to at least one of a direct current (DC), an alternating current (AC), and a pulsed current which are electrotherapeutic currents usable for microcurrent therapy through the third input data input by the user directly or in remote control.

As a result, in the graph of FIG. 3, even though it has been illustrated that the generation types of the microcurrent 400 and the aware stimulus 500 are the pulsed currents, the generation types may be changed to the direct current or the alternating current according to information of the third input data input to the controller 110.

In the present disclosure, the direct current may be at least one of a continuous direct current generated for 1 second or more without changing a polarity to positive (+) or negative (−) electrode, a reversed direct current of which the polarity is changed to positive (+) or negative (−) electrode after generated for 1 second or more, an interrupted direct current in which the flow of the current is temporarily stopped so as to be interrupted at an interval of 1 second or more after the continuous direct current is generated, a ramped direct current which gentle ascending and descending occur at the start and end portions of the current, and a ramped, reversed direct current of which the polarity is changed after the ramped direct current is generated for 1 second or more.

In the present disclosure, the alternating current may be at least one of a symmetrical alternating current with the same current type while a flowing direction of electrons is continuously changed in one period, and an asymmetrical alternating current of which the current type varies in one period, unlike the symmetrical alternating current.

In the present disclosure, the pulsed current may be at least one of a single-phase pulsed current having a characteristic of a positive or negative electrode in which charged particles are periodically interrupted for a time of 1 msec or 1 μsec or less in one period and the polarity is not changed unlike the direct current and the alternating current, and a bi-phase pulsed current having alternately characteristics of the positive and negative electrodes through a periodic change of the polarity in one period unlike the single-phase pulsed current.

When setting the generation types of the microcurrent 400 and the aware stimulus 500 through the input of the third input data, the controller 110 first sets the generation type of the microcurrent 400, and when the generation type of the microcurrent 400 is set, the controller 110 sets the generation type of the aware stimulus 500 with a different amplitude and/or a different wavelength from the generation type of the microcurrent 400.

When describing a specific example of the process of setting the generation types of the microcurrent 400 and the aware stimulus 500 with reference to FIG. 3, the controller 110 may set the generation type of the aware stimulus 500 to a pulsed current with a different amplitude and/or a different wavelength from the microcurrent 400 when setting the generation times and periods of the microcurrent 400 and the aware stimulus 500 according to the input of the second input data and then setting the generation type of the microcurrent 400 to the pulsed current through the input of the third input data.

In addition, as another specific example of the process of setting the generation types of the microcurrent 400 and the aware stimulus 500, the controller 110 may set the generation type of the aware stimulus 500 to an alternating current with a different amplitude and/or a different wavelength from the microcurrent 400 when setting the generation times and periods of the microcurrent 400 and the aware stimulus 500 according to the input of the second input data and then setting the generation type of the microcurrent 400 to the pulsed current through the input of the third input data.

That is, it is preferable that it is understood that the aware stimulus 500 described in the present disclosure is at least one of a direct current, an alternating current, and a pulsed current having a different amplitude and/or a different wavelength from the microcurrent 400.

As the graph shown in FIG. 3, the controller 110 sets the generation types of the microcurrent 400 and the aware stimulus 500 so that a peak amplitude and a peak-to-peak amplitude of the aware stimulus 500 are relatively larger than a peak amplitude and a peak-to-peak amplitude of the microcurrent 400.

At this time, the peak amplitude means a maximum current induced from a single phase of the pulse, and the peak-to-peak amplitude means a maximum current that sums the peak amplitude of each phase contained within one period of a bi-phase pulse or the aware stimulus 500.

It is preferable to consider a virtual value amplitude of the aware stimulus 500 when the controller 100 sets the peak amplitude and the peak-to-peak amplitude of the aware stimulus 500 so that the aware stimulus 500 capable of being aware by the user is applied to the body tissue of the user to which the aware stimulus electrode 142 is attached.

At this time, the virtual value amplitude means a magnitude of an effective current for the aware stimulus 500 transmitted to the body tissue of the user and the effective current means a virtual value determined in a quantity of heat generated in a resistance caused by the same degree of current.

That is, it is preferred that the controller 110 sets the peak amplitude and the peak-to-peak amplitude of the aware stimulus 500 so that the virtual value amplitude of the aware stimulus 500 is relatively larger than that of the microcurrent 400 so that the user may easily determine whether the microcurrent therapy is performed through the aware stimulus 500.

The controller 110 sets the generation type of the aware stimulus 500 so that a start period and an end period of the aware stimulus 500 are generated with a different amplitude and/or a different wavelength from the remaining periods of the aware stimulus 500.

At this time, the start period of the aware stimulus 500 means one period of the aware stimulus 500 which is first generated after the microcurrent therapy starts as the aware stimulus 500 is separated into plural and the end period of the aware stimulus 500 means one period of the aware stimulus 500 which is last generated before the microcurrent therapy ends. As a result, the user may be easily aware of the start and end of the microcurrent therapy through the start period of the aware stimulus 500 and the end period of the aware stimulus 500.

In addition, the start period and the end period of the aware stimulus 500 are set so that the peak amplitude and the peak-to-peak amplitude are relatively larger than those of the remaining periods of the aware stimulus 500 by the controller 110 and as a result, set so that the virtual value amplitude is larger than that of the remaining periods of the aware stimulus 500, so that the user may easily determine the start and the end of the microcurrent through the aware stimulus 500.

In addition, the start period and the end period of the aware stimulus 500 may have different virtual value amplitudes therebetween in order to achieve the purpose for easily notifying the start of the microcurrent therapy to the user or the purpose for easily notifying the end of the microcurrent therapy to the user.

That is, in order to easily notify the start of the microcurrent therapy to the user based on the start period of the aware stimulus 500, the start period of the aware stimulus 500 may have a virtual value amplitude larger than the end period of the aware stimulus 500. However, for the purpose of easily notifying the end of the microcurrent therapy to the user, the end period of the aware stimulus 500 may have a virtual value amplitude larger than the start period of the aware stimulus 500.

At this time, when the end of the microcurrent therapy is easily notified to the user, the user aware microcurrent therapy device 100 may prevent the user from wearing the user aware microcurrent therapy device 100 for a long time while the microcurrent therapy ends.

Hereinafter, as compared with the first exemplary embodiment of the present disclosure, a user aware microcurrent therapy device 200 according to a second exemplary embodiment of the present disclosure in which the generation types of the microcurrent 400 and the aware stimulus 500 are modified will be described in detail.

Figure 4:
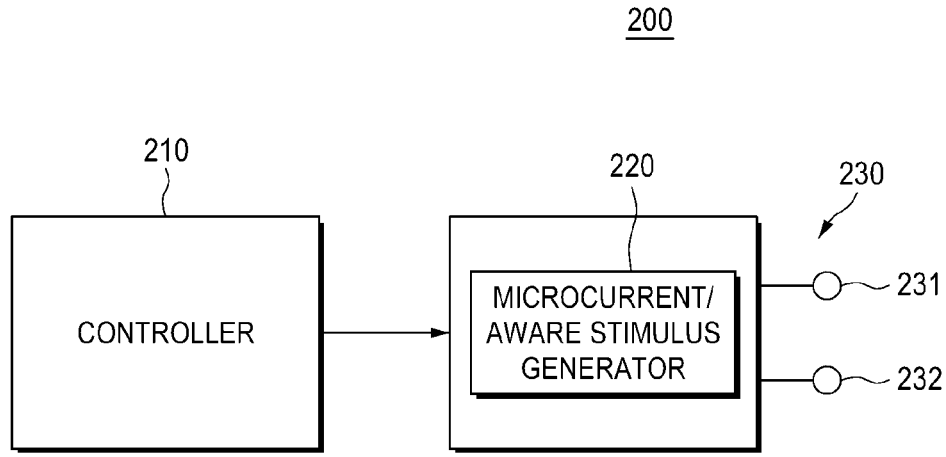
FIG. 4 is a schematic diagram of a user aware microcurrent therapy device according to a second exemplary embodiment of the present disclosure.

FIG. 4 is a schematic diagram of a user aware microcurrent therapy device according to a second exemplary embodiment of the present disclosure.

Referring to FIG. 4, the user aware microcurrent therapy device 200 according to the second exemplary embodiment of the present disclosure includes a controller 210, a microcurrent/aware stimulus generator 220, and a plurality of electrodes 230.

Since the controller 210 is different only in reference numeral from the controller 110 described in the first exemplary embodiment of the present disclosure, but is the same in the configuration, and thus, the detailed description will be omitted for convenience.

The microcurrent/aware stimulus generator 220 is to combine the microcurrent generator 120 and the aware stimulus generator 130 described in the first exemplary embodiment of the present disclosure into one. The microcurrent/aware stimulus generator 220 generates a specific type of microcurrent 400 according to the second and third input data input to the controller 210 for a predetermined time and generates a specific type of aware stimulus 500 alternately with the microcurrent 400 for a predetermined time.

At this time, the microcurrent 400 and the aware stimulus 500 are separated into a plurality of periods as the graph shown in FIG. 2 and may be set to at least one of a direct current, an alternating current, and a pulsed current which are electrotherapeutic currents usable for microcurrent therapy by the controller 210 as the graph shown in FIG. 3.

The plurality of electrodes 230 may consist of a microcurrent electrode 231 and an aware stimulus electrode 232.

The microcurrent electrode 231 is connected with the microcurrent/aware stimulus generator 220 so that the microcurrent 400 generated by the microcurrent/aware stimulus generator 220 flows. As a result, when the microcurrent electrode 231 is attached to a user's body part to receive the microcurrent therapy, the microcurrent electrode 231 applies a specific type of microcurrent 400 separated into the plurality of periods to the body part.

The aware stimulus electrode 232 is connected with the microcurrent/aware stimulus generator 220 so that the aware stimulus 500 generated by the microcurrent/aware stimulus generator 220 flows. As a result, when the aware stimulus electrode 232 is attached to the remaining body parts except for the user's body part attached with the microcurrent electrode 231, the aware stimulus electrode 232 applies a specific type of aware stimulus 500 separated into the plurality of periods to be generated alternately with the microcurrent 400 to the body part.

Through the microcurrent electrode 231 and the aware stimulus electrode 232, while the user receives the microcurrent therapy by the microcurrent 400, the user may determine whether the microcurrent therapy is performed through the aware stimulus 500 generated alternately with the microcurrent 400.

Hereinafter, as compared with the first exemplary embodiment of the present disclosure, a user aware microcurrent therapy device 300 according to a third exemplary embodiment of the present disclosure in which the generation types of the microcurrent 400 and the aware stimulus 500 and the form of the plurality of electrodes 140 are modified will be described in detail.

Figure 5:
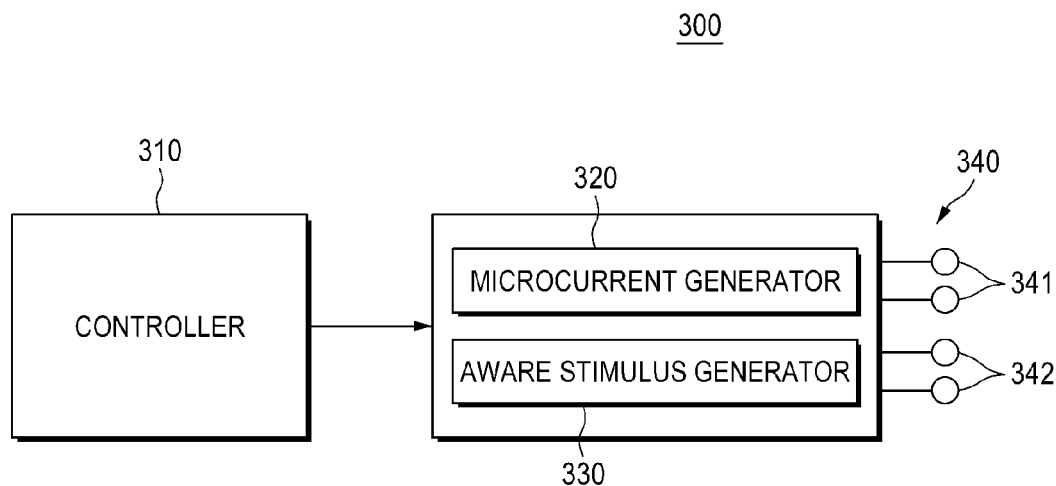
FIG. 5 is a schematic diagram of a user aware microcurrent therapy device according to a third exemplary embodiment of the present disclosure.
Figure 6:
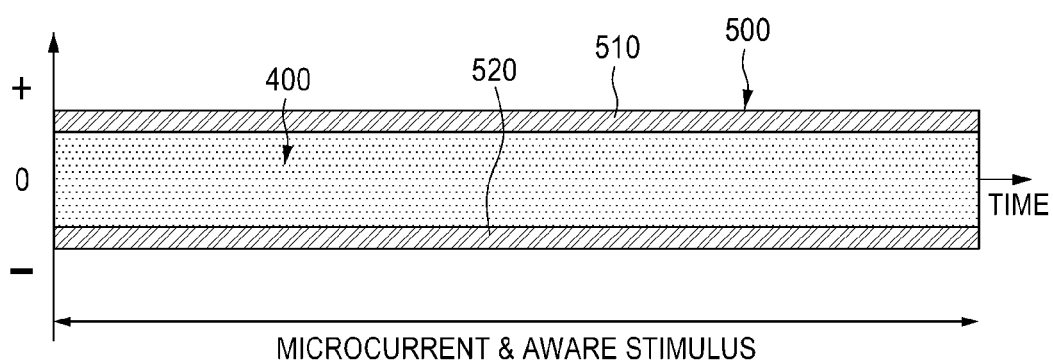
FIG. 6 is a graph showing periods of a microcurrent and an aware stimulus which are generated in one period according to the third exemplary embodiment of the present disclosure.
Figure 7:
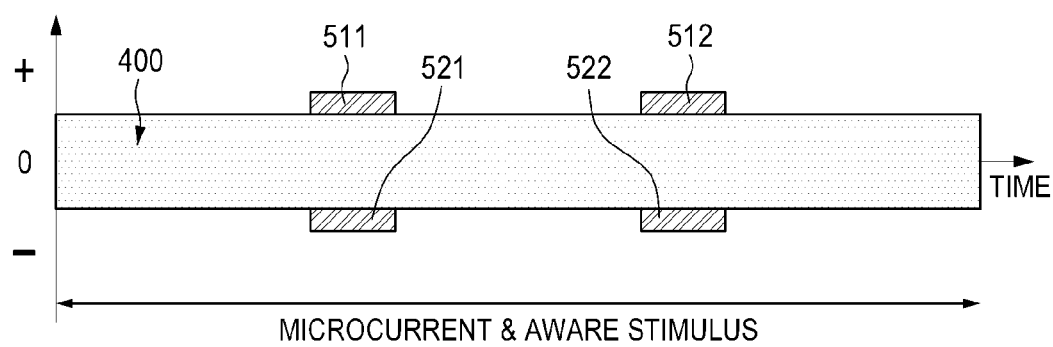
FIG. 7 is a graph showing periods of a microcurrent and aware stimuli separated into a plurality of periods according to the third exemplary embodiment of the present disclosure.

FIG. 5 is a schematic diagram of a user aware microcurrent therapy device according to a third exemplary embodiment of the present disclosure, FIG. 6 is a graph showing periods of a microcurrent and an aware stimulus generated in one period according to the third exemplary embodiment of the present disclosure, and FIG. 7 is a graph showing periods of a microcurrent and aware stimuli separated into a plurality of periods according to the third exemplary embodiment of the present disclosure.

Referring to FIG. 5, a user aware microcurrent therapy device 300 according to the third exemplary embodiment of the present disclosure includes a controller 310, a microcurrent generator 320, an aware stimulus generator 330 and a plurality of electrodes 340.

Since the controller 310 is different only in reference numeral from the controller 110 described in the first exemplary embodiment of the present disclosure, but is the same in the configuration, and thus, the detailed description will be omitted for convenience.

The microcurrent generator 320 is connected to the controller 310 and generates a specific type of microcurrent 400 for a predetermined time according to the second and third input data input to the controller 210.

In addition, the microcurrent generator 320 generates the microcurrent 400 in one period for a predetermined time as the graphs shown in FIGS. 6 and 7 according to the second and third input data.

In addition, as the graphs shown in FIGS. 6 and 7, the microcurrent generator 320 generates the microcurrent 400 in a wavelength form in which the polarity is periodically changed from positive to negative or from negative to positive for one period.

The aware stimulus generator 330 is connected to the controller 310 and generates a specific type of aware stimulus 500 for a predetermined time according to the second and third input data input to the controller 210.

Further, the aware stimulus generator 330 may generate the aware stimulus 500 in one period for the same time as the microcurrent 400 as the graph shown in FIG. 6 according to the second and third input data. At this time, since the aware stimulus 500 is generated in one period, after the microcurrent therapy starts, the pulse for a specific time may notify the start of the microcurrent therapy by varying an amplified and/or wavelength of the remaining pulses, and before the microcurrent therapy ends, the pulse for a specific time may notify the end of the microcurrent therapy by varying an amplified and/or wavelength of the remaining pulses.

As a specific example when the aware stimulus generator 330 generates the aware stimulus 500 in one period, when the second and third input data are input to the controller 310, the aware stimulus generator 330 may generate the aware stimulus 500 of which the polarity is periodically changed to an aware stimulus 510 of a positive electrode and an aware stimulus 520 of a negative electrode for the same time as the microcurrent 400.

Meanwhile, if the aware stimulus generator 330 does not generate the aware stimulus 500 in one period after the second and third input data are input, as the graph shown in FIG. 7, the aware stimulus generator 330 may separate the aware stimulus 500 into a plurality of periods and generate the aware stimulus 500 separated into the plurality of periods for a predetermined time.

As a specific example when the aware stimulus generator 330 generates the aware stimulus 500 in a plurality of periods, when the second and third input data are input to the controller 310, the aware stimulus generator 330 may generate the aware stimulus 500 of which the polarity is periodically changed to a first aware stimulus 511 of the positive electrode and a first aware stimulus 521 of the negative electrode within a time when the microcurrent 400 is generated as a start period of the aware stimulus 500 for notifying the start of the microcurrent therapy. In addition, the aware stimulus generator 330 may generate the aware stimulus 500 of which the polarity is periodically changed to a second aware stimulus 512 of the positive electrode and a second aware stimulus 522 of the negative electrode which are separated from the first aware stimuli 511 and 521 within the time when the microcurrent 400 is generated through a short circuit as the end period of the aware stimulus 500 for notifying the end of the microcurrent therapy to the user.

Furthermore, the aware stimulus generator 330 may generate the first aware stimuli 511 and 521 of the positive and negative electrodes and the second aware stimuli 512 and 522 of the positive and negative electrodes which have different virtual value amplitudes by the controller 310 to achieve the purpose for easily notifying the start of the microcurrent therapy to the user or the purpose for easily notifying the end of the microcurrent therapy to the user.

At this time, the first aware stimuli 511 and 521 of the positive and negative electrodes may have a virtual value amplitude larger than the second aware stimuli 512 and 522 of the positive and negative electrodes to achieve the purpose for easily notifying the start of the microcurrent therapy to the user. However, the second aware stimuli 512 and 522 of the positive and negative electrodes may have a virtual value amplitude larger than the first aware stimuli 511 and 521 of the positive and negative electrodes for the purpose of easily notifying the end of the microcurrent therapy to the user.

The plurality of electrodes 340 may consist of a plurality of microcurrent electrodes 341 and a plurality of aware stimulus electrodes 342.

The plurality of microcurrent electrodes 341 are two electrodes connected with the microcurrent generator 320, respectively, so that the microcurrent 400 generated by the microcurrent generator 320 flows. As a result, when the microcurrent electrodes 341 are attached to a user's body part to receive the microcurrent therapy, the microcurrent electrodes 341 apply a specific type of microcurrent 400 generated in one period to the body part.

The plurality of aware stimulus electrodes 342 are two electrodes connected with the aware stimulus generator 330, respectively, so that the aware stimulus 500 generated by the aware stimulus generator 330 flows. As a result, when the aware stimulus electrodes 342 are attached to the remaining body parts except for the user's body part attached with the plurality of microcurrent electrodes 341, the plurality of aware stimulus electrodes 342 apply a specific type of aware stimulus 500 generated in one period or the plurality of periods to the body part.

Further, as the plurality of aware stimulus electrodes 342 consists of two electrodes, one electrode may apply a specific type of aware stimulus 500 generated in one period, and the other electrode may apply a specific type of aware stimulus 500 generated in the plurality of periods.

Meanwhile, in the plurality of aware stimulus electrodes 342, one electrode may apply the aware stimulus 500 at the start period of the aware stimulus 500 and may apply the aware stimulus 500 at the end period of the aware stimulus 500.

Through the plurality of microcurrent electrodes 341 and the plurality of aware stimulus electrodes 342, while the user receives the microcurrent therapy by the microcurrent 400, the user may determine whether the microcurrent therapy is performed through the aware stimulus 500 generated in one period or a plurality of periods within the time when the microcurrent 400 is generated.

Detailed descriptions of the preferred exemplary embodiments of the present disclosure disclosed as described above are provided so as for those skilled in the art to implement and execute the present disclosure. The present disclosure has been described with reference to the preferred exemplary embodiments, but those skilled in the art will understand that the present disclosure can be variously modified and changed without departing from the scope of the present disclosure. For example, those skilled in the art may use the respective components disclosed in the exemplary embodiments by combining the respective components with each other. Therefore, the present disclosure is not limited to the exemplary embodiments described herein, but intends to grant the widest range which is coherent with the principles and new features disclosed herein.

The present disclosure may be embodied in other specific forms without departing from the spirit and essential characteristics of the present disclosure. Accordingly, the aforementioned detailed description should not be construed as restrictive in all terms and should be exemplarily considered. The scope of the present disclosure should be determined by rational construing of the appended claims and all modifications within an equivalent scope of the present disclosure are included in the scope of the present disclosure. The present disclosure is not limited to the exemplary embodiments described herein, but intends to grant the widest range which is coherent with the principles and new features presented herein. Further, the claims that are not expressly cited in the claims are combined to form an exemplary embodiment or be included in a new claim by an amendment after the application.

That which is claimed is:

1. A user aware microcurrent therapy device comprising:
a controller configured to input:
first input data for turning on/off power,
second input data for setting generation times and periods of a microcurrent for microcurrent therapy and an aware stimulus which notifies a user of generation of the microcurrent, and
third input data for setting generation types of the microcurrent and the aware stimulus;
a microcurrent generator which is connected to the controller to generate a specific type of microcurrent separated into a plurality of periods according to the second and third input data input to the controller for a predetermined time;
an aware stimulus generator which is connected to the controller to generate a specific type of aware stimulus separated into the plurality of periods according to the second and third input data input to the controller alternately with the microcurrent for the predetermined time; and
a plurality of electrodes which applies the microcurrent generated by the microcurrent generator and the aware stimulus generated by the aware stimulus generator to the user when the plurality of electrodes is adapted to be attached to a part of the user's body,
wherein the aware stimulus is a current which the user who receives the microcurrent therapy will be aware of and the current is applied to the body of the user, and
wherein the controller sets the generation type of the aware stimulus so that a start period of the aware stimulus for notifying a start of the microcurrent therapy and an end period of the aware stimulus for notifying an end of the microcurrent therapy are generated with different amplitudes and/or different wavelengths from remaining periods of the aware stimulus, based on a case where the aware stimulus is separated into the plurality of periods.

2. The user aware microcurrent therapy device of claim 1, wherein the controller sets the generation types of the microcurrent and the aware stimulus to at least one of: a direct current, an alternating current, or a pulsed current when the third input data is input.

3. The user aware microcurrent therapy device of claim 2, wherein the controller first sets the generation type of the microcurrent through the input of the third input data and sets the generation type of the aware stimulus with a different amplitude and/or a different wavelength from the generation type of the microcurrent when the generation type of the microcurrent is set.

4. The user aware microcurrent therapy device of claim 1, wherein the controller sets the generation type of the aware stimulus so that a virtual value amplitude of the start period of the aware stimulus is different from that of the end period of the aware stimulus.

5. The user aware microcurrent therapy device of claim 1, wherein the controller sets the generation times and periods of the microcurrent and the aware stimulus so that the period of the microcurrent is generated earlier than the period of the aware stimulus when the microcurrent therapy starts in a case where the second input data is input.

6. The user aware microcurrent therapy device of claim 5, wherein the controller sets the generation times and periods of the microcurrent and the aware stimulus so that the end period of the aware stimulus for notifying that the microcurrent therapy ends among the plurality of periods of the aware stimulus ends and then the microcurrent therapy ends, when the second input data is input.

7. The user aware microcurrent therapy device of claim 1, wherein the controller sets the generation times and periods of the microcurrent and the aware stimulus so that the periods of the microcurrent and the periods of the aware stimulus are gradually increased as the microcurrent therapy is performed.

8. The user aware microcurrent therapy device of claim 1, wherein the controller sets the generation times and periods of the microcurrent and the aware stimulus so that the periods of the microcurrent and the periods of the aware stimulus are gradually decreased as the microcurrent therapy is performed.

* * * * *